United States Patent [19]

Raines et al.

[11] 4,173,223
[45] Nov. 6, 1979

[54] CHAMBER ASSEMBLY FOR INFUSION AND TRANSFUSION APPARATUS

[75] Inventors: Kenneth C. Raines; Robert J. LeFevre, both of Bethlehem, Pa.

[73] Assignee: National Patent Development Corporation, New York, N.Y.

[21] Appl. No.: 843,064

[22] Filed: Oct. 17, 1977

[51] Int. Cl.$^2$ ............................................. A61M 5/16
[52] U.S. Cl. ................................................ 128/214 C
[58] Field of Search ............ 128/214 R, 214 C, 214 F, 128/214 Z

[56] References Cited

U.S. PATENT DOCUMENTS

| | | | |
|---|---|---|---|
| 2,664,085 | 12/1953 | Ryan | 128/214 C |
| 3,021,841 | 2/1962 | Burke | 128/214 C |
| 3,521,635 | 7/1970 | Koehn | 128/214 C |
| 4,055,176 | 10/1977 | Lundquist | 128/214 C |

*Primary Examiner*—Dalton L. Truluck
*Attorney, Agent, or Firm*—Shoemaker and Mattare, Ltd.

[57] ABSTRACT

A chamber assembly for infusion and transfusion apparatus comprising a drip chamber having a pump chamber and an observation chamber connected together and connecting a tubing adaptor to a piercing device assembly. The cross-sectional area of the observation chamber is smaller than the cross-sectional area of the pump chamber and the observation chamber is short relative to the pump chamber. Changes in pressure in the pump chamber are transmitted through the observation chamber faster than such pressure changes are transmitted through the pump chamber because of the difference in length of the two chambers. The difference in cross-sectional areas of the two chambers causes the pressure wave in the observation chamber to be more uniform than that wave is in the pump chamber. The assembly including the observation and pump chambers accurately controls the flow rate of fluid into the tubing, so that only a single drop is present in the observation chamber at any one time.

11 Claims, 5 Drawing Figures

U.S. Patent  Nov. 6, 1979  4,173,223
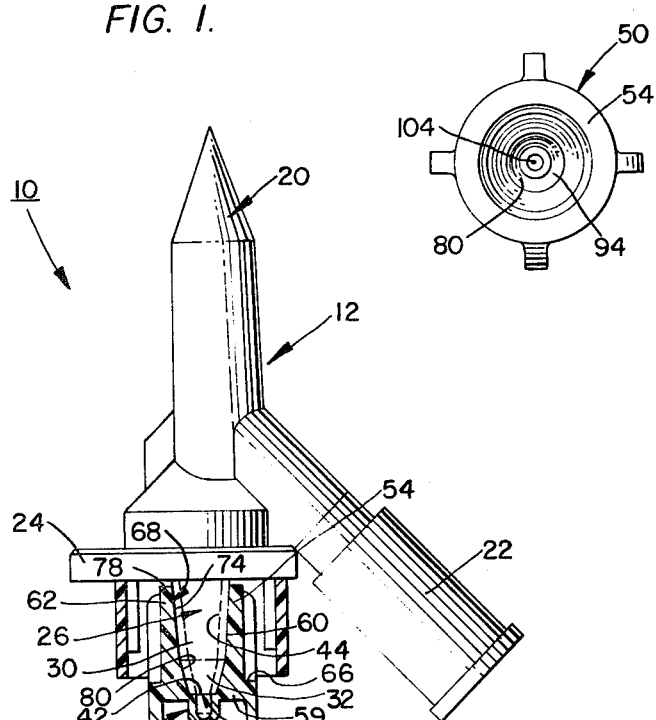
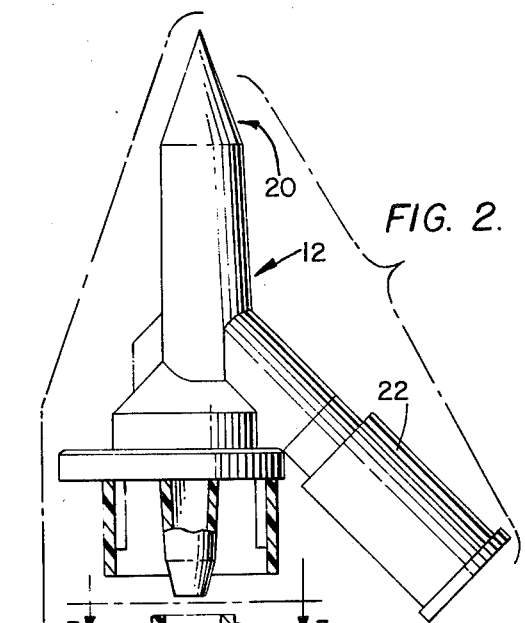
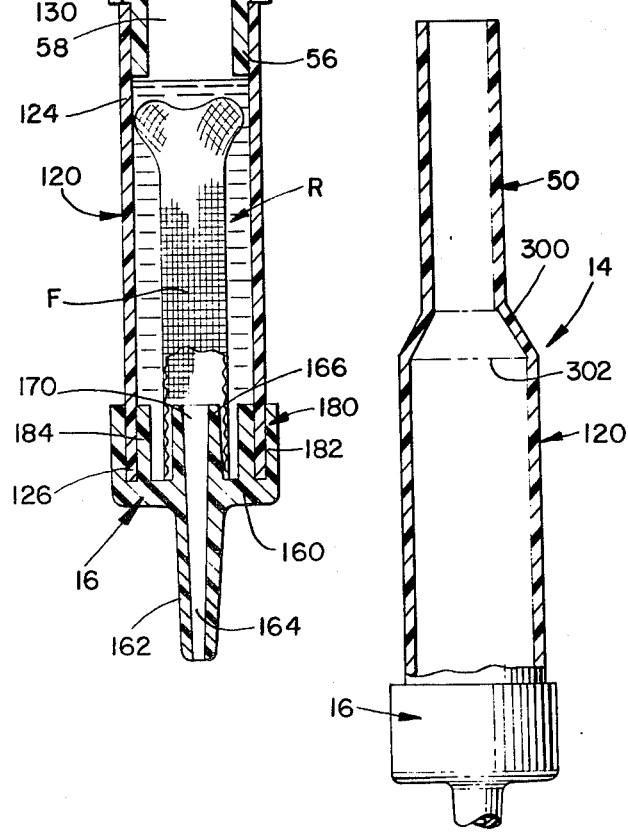
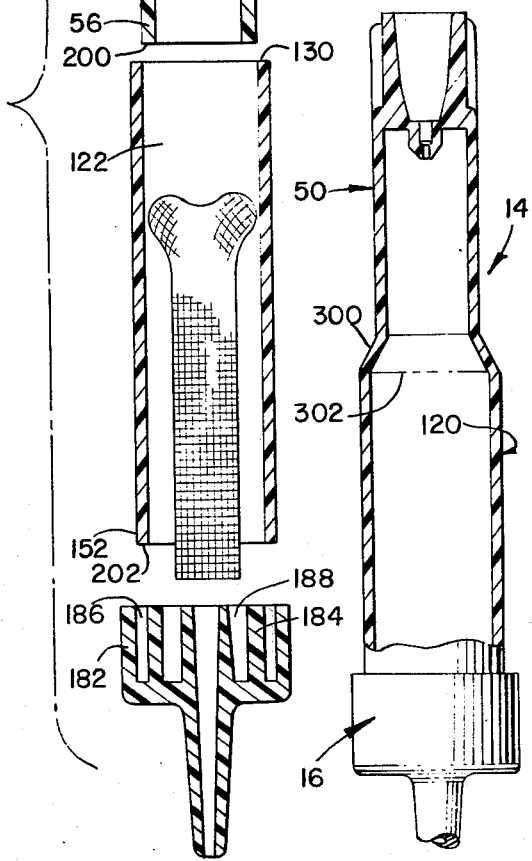

CHAMBER ASSEMBLY FOR INFUSION AND TRANSFUSION APPARATUS

BACKGROUND OF THE INVENTION

The present invention relates, in general, to infusion and transfusion apparatus, and more particularly, to flow control devices for infusion and transfusion apparatus.

Control of the flow rate of fluid in infusion and transfusion apparatus is one very important consideration in constructing such apparatus. The prior art discloses various means for effecting such flow control. Manual flow regulators are quite common in the prior art, and such regulators often use clamps or other such manually operated devices to control flow. Such manually controlled regulators are convenient, but do not provide the flow control accuracy required in modern medicine. Recently, electronically controlled regulators have been utilized to control flow in infusion and transfusion systems. Examples of such electronic systems are disclosed in LeFevre, et al. U.S. Pat. No. 4,038,981 and Burke, et al. U.S. Pat. No. 4,038,982. These patents have a complete disclosure of an electronic system, and reference is made thereto for such description. Such electronic regulators produce exceptionally accurate and reliable control of the rate with which fluid is administered to a patient.

It is noted that infusion and transfusion systems utilize a means for connecting tubes to the fluid source which comprises at least two main elements, a piercing device which is attached directly to the source of fluid, and a drip chamber which transfers the fluid from the piercing device to the tubing via tubing connectors. A degree of mechanical control of the fluid flow in an infusion and transfusion apparatus can be exercised in the drip chamber portion of the apparatus. Flow control means, such as metering orifices and the like, are often used.

It has been observed that air in a drip chamber acts as a "cushion" and exerts a strong influence on fluid flowing into the chamber through an inlet port means in that chamber. The air located adjacent the inlet port means determines the back pressure on that port, which, along with the pressure of the fluid upstream of the port, determines the pressure differential established across the port. The pressure differential, in turn, determines the amount and character of the flow through the port means. Thus, if the fluid pressure existing upstream of the inlet port is fairly constant, flow through the port responds in rate and character to changes in the back pressure, or that pressure in the drip chamber existing immediately adjacent the port. Such pressure changes generally only occur as a result of influences exerted on the drip chamber from the system downstream of the drip chamber. Thus, flow demands made on the solution source from the system are transmitted to the source via pressure disturbances in the drip chamber. It is noted that propagation of a pressure wave through a medium is subject to damping effects, and thus the flow demands of the overall system are subject to being damped by the air cushion existing in the drip chamber, and accordingly, these flow demands are not accurately and precisely transmitted to the fluid source by the drip chamber, thereby resulting in the above-discussed inaccuracies which render known drip chamber configurations inadequate for use in conjunction with the extremely accurate and precise electronic flow control systems.

This phenomenon can be stated in hydraulic terms by viewing the cushion of air in the drip chamber as a damping means which tends to damp out pressure perturbations transmitted through the drip chamber. During administration of fluid to a patient, fluid is withdrawn from the source in response to pressure perturbations transmitted through the drip chamber from the tubing adaptor. Thus, a large air cushion with the attendant pressure perturbation damping effects thereof may tend to vitiate the precision with which the drip chamber fluid feed mechanism responds to the flow demands placed thereon by the overall system.

In the referenced LeFevre and Burke patents, for example, the air volume in the drip chamber below the metering orifice is approximately 2 cc which has often resulted in double or triple drops from a 60 drop per milliliter orifice during a single cycle of the electronic flow control apparatus. In the referenced patents, the flow control mechanism utilizes an electronic timing device which is triggered by a droplet traversing the drip chamber. Such multiple drop formations may therefore cause electronic control to mismanage the fluid flow through the apparatus or to malfunction during the control cycle. Therefore, while the presently known drip chamber formations and configurations are sufficiently accurate for most applications, the extreme precision of the electronic flow controls, such as those controls disclosed in the referenced patents, requires much faster response and greater exactness than can be provided by known drip chambers.

A further function of the drip chamber portion of the infusion and transfusion apparatus is in priming the system, that is, initiating flow from the source of fluid. This function is generally performed by manually manipulating a flexible portion of the drip chamber to create a suction on the fluid source. Therefore, manufacture of a drip chamber has several constraints placed thereon to account for this function. The flexible portion of the drip chamber must be large enough to be easily manipulated during the priming operation, yet the overall drip chamber must be small enough to prevent generation of an air cushion adjacent the inlet port, which air cushion is of sufficient size to produce multiple drops, as above discussed. Furthermore, the pump chamber can serve as a reservoir of fluid to prevent interruption of flow during the initial moments after an empty bottle situation, and should be manufactured to account for this function as well.

The fore end of the drip chamber is assembled with a piercing device, and thus should be somewhat rigid to facilitate easy coupling of the drip chamber and the piercing device assembly.

Therefore, an ideal drip chamber should monitor flow from the source of fluid with an accuracy commensurate with electronic monitoring systems, yet be amenable to efficient manufacture and use.

SUMMARY OF THE INVENTION

The drip chamber embodying the teachings of the present invention controls flow from the source with an accuracy commensurate with electronic flow regulators, and is efficiently manufactured and used.

The overall apparatus includes a piercing point assembly for connection to a source of fluid and a tubing adaptor fluidly and mechanically coupled to the piercing point assembly by a drip chamber. The drip chamber includes an observation chamber formed of rigid materials, such as plastic or the like, coupled to the piercing point assembly and a pump chamber formed of flexible material having a memory coupling the observation chamber to the tubing adaptor. A filter is positioned in the pump chamber to filter fluid passing from the drip chamber into the tubing connected thereto by the tubing adaptor. A flow entrance means, such as an inlet port, or a metering orifice, is positioned within the observation chamber and fluidly couples the observation chamber to the piercing point assembly.

Flow into the observation chamber via the entrance means is in droplet form and can be controlled according to the conditions existing in the observation chamber. The volume of the observation chamber determines the size of the air cushion in that chamber, and that air cushion, in turn, exerts back pressure on the inlet port and controls the flow of fluid from the fluid inlet port into the drip chamber. Flow changes, preferably from a no-flow condition to a finite flow condition, result from pressure perturbations in the drip chamber which cause a change in the back pressure exerted upon the inlet port. As above discussed, flow demands placed on the fluid source by the overall system are transmitted through the drip chamber in the form of pressure perturbations. Accordingly, the faster and more accurately such pressure perturbations are transmitted to the inlet port, the faster and more accurately flow through such inlet port can react to the system demands.

Such rapid and precise pressure perturbation transmission through the drip chamber can be accomplished in many ways, but there are special constraints of expeditious manufacture and use placed on the construction of a drip chamber for use in an infusion and transfusion apparatus. For example, not only must the drip chamber transmit pressure perturbations thereacross precisely and rapidly, such chamber must be usable as a pump to prime the system during initial assembly. Thus, some portion of the drip chamber must be manufactured to accomplish this function. Furthermore, the pump portion of the drip chamber must be amenable to expeditious use once assembled, and therefore must be conveniently sized, placed and configured for this purpose.

To achieve the result of rapid and accurate pressure perturbation transmission while still producing the desired functions for the drip chamber, the drip chamber embodying the teachings of the present invention includes an observation chamber connected to the piercing point assembly which has a length and cross-sectional area, and hence a volume, less than the length and cross-sectional area, and hence the volume, of the pump chamber connecting that observation chamber to the tubing via the tubing adaptor.

The pump and observation chamber sections are coupled together, and thus there is an abrupt volume change within the drip chamber occurring at the joint between these two sections. The volume change, as used herein, refers to the change in cross-sectional area, as cross-sectional area is equivalent to volume per unit length of the section.

In use, the pump section or portion is used to prime the system, and is operated to draw fluid from the source through the inlet port means into the observation chamber until fluid fills the pump chamber section to the joint whereat the pump and observation chamber sections are joined and whereat the abrupt cross-sectional area change occurs. This fluid forms a reservoir from which fluid is withdrawn according to system demands.

As fluid is withdrawn from the reservoir, the level thereof drops thereby sending a pressure perturbation upwardly into the observation chamber. Due to the difference in cross-sectional areas, or volumes, of the two chambers, the pressure perturbation is stronger in the observation chamber than it is in the pump chamber, which is larger than the observation chamber, and the volume of air in the observation chamber does not cushion that pressure perturbation as much as it would if the two chambers were of equal cross-sectional area.

During the withdrawal operation, the pressure perturbation is in the form of a pressure decrease, and thus manifests itself as a decrease in back pressure at the inlet port in the observation chamber, thereby prompting the flow of fluid therefrom. The inlet port is in a configuration such that flow therethrough is in droplet form.

When the droplet reaches the fluid reservoir, the reservoir level again rises and sends out a further pressure perturbation which is transmitted to the observation chamber in the form of an increase in pressure. The increase in pressure brings the pressure in the drip chamber back up to the pressure wherein a no-flow condition is established across the inlet port and is, therefore, not a pressure "wave" or "perturbation" per se. Again, the difference is cross-sectional areas of the two chambers causes this pressure "wave" to be propagated through the observation chamber with greater intensity than if that chamber and the pump chamber were of equal size. The pressure "perturbation" impinges on the inlet port means in the form of a back pressure "increase", thereby causing flow through the inlet port to cease. Cessation of flow continues until a further demand on the overall system causes the reservoir level to again drop, whereupon the just-discussed operation re-occurs.

It is noted that by filling the pump chamber to the joint, or the base of the observation chamber, pressure perturbations caused by movement of the liquid level in the reservoir are transmitted directly into the observation chamber without traversing any significant length of the pump chamber. Such positioning thus effectively prevents any damping of the pressure perturbation by the relatively large cross-sectional area of the pump chamber.

The length of the observation chamber is selected so that the pressure perturbations traverse the length of that chamber in time to create and/or shut off flow through the inlet port in synchronization with the overall system flow regulators, especially the electronic flow regulators which may mismanage flow or malfunction if more than one drop is created in the observation chamber for a one drop withdrawal from the drip chamber.

In the aforementioned patents, the drip chamber has a constant cross-sectional area and an air volume of 2 cubic centimeters below the inlet port means in the observation chamber, and, due to the just-discussed hydraulic effects, multiple drops are often formed during one cycle of the electronic timer. As the timer is triggered by droplets being formed in the drip chamber, such multiple droplet formation has proved to be somewhat undesirable and vitiates to some degree the accuracy of the electronic flow control equipment.

Accordingly, in the preferred embodiment of the present invention, the observation chamber of the present invention has a volume of 0.65 cubic centimeters which produces a single drop from a 60 drop orifice. The chamber has a rigid observation chamber section and a flexible pump chamber section which are coupled together during assembly of the overall system. The separate nature of the observation and pump chamber sections facilitates expeditious manufacture and use of those elements.

OBJECTS OF THE INVENTION

It is, therefore, a main object of the present invention to provide a drip chamber which monitors flow in a transfusion and infusion apparatus with an accuracy commensurate with an electronic flow regulator.

It is another object of the present invention to provide a drip chamber which is easily and expeditiously manufactured.

It is a further object of the present invention to provide a drip chamber which is easily assembled and used.

It is yet another object of the present invention to provide a drip chamber which produces a reservoir of fluid for use during an empty bottle condition.

These together with other objects and advantages which will become subsequently apparent reside in the details of construction and operation as more fully hereinafter described and claimed, reference being had to the accompanying drawings forming part thereof, wherein like reference numerals refer to like parts throughout.

BRIEF DESCRIPTION OF THE DRAWINGS

FIG. 1 is an elevation view of the apparatus embodying the teachings of the present invention.

FIG. 2 is a separated elevation view of the apparatus embodying the teachings of the present invention.

FIG. 3 is a view taken along line 3—3 of FIG. 2.

FIGS. 4 and 5 show alternative embodiments of the device embodying the teachings of the present invention.

DETAILED DESCRIPTION OF THE INVENTION

Shown in FIG. 1 is a connecting assembly 10 embodying the teachings of the present invention. The assembly 10 has a piercing device assembly 12 serially and fluidly connected to a drip chamber assembly 14, which, in turn, is serially and fluidly connected to a tubing adaptor 16.

The piercing device assembly is of known construction and includes a piercing point 20, an air inlet section 22, and a coupling collar section 24 depending downwardly from the base of the piercing device assembly 12 in the operative orientation as shown in FIG. 1. The piercing point 20 is inserted into a source of fluid (not shown), and fluid is conducted into the drip chamber assembly through the piercing point assembly. The assembly 20 includes a spike which depends downwardly from the piercing device assembly and includes a frusto-conical base section 30 having the base thereof mounted on the piercing assembly, and a frusto-conical transition section 32 having the base thereof mounted on the frustum of the base section. A port 40 is defined in the frustum of the transition section. The port can include a metering orifice 42 which is sized to flow 20 drops per milliliter, or the like therethrough. The spike is hollow and thus a stepped bore 44 is defined therethrough to fluidly connect the port 40 with the fluid path (not shown) within the piercing assembly for conducting fluid out of the source.

The drip chamber assembly includes an observation chamber 50 which has a tubular body 52 having an upper end 54 and a lower end 56. The body has a blind ended bore 58 defined therein which is open at end 56 and closed at end 54 by a bulkhead 59. A connector section 60 is located on end 54 and includes a tubular body 62 extending upwardly from end 54 and having an outer diameter less than the outer diameter of the tubular body 52 to define at end 54 a shoulder 66. The connector section is hollow and has a stepped bore 68 defined axially therethrough and which includes a frusto-conical base receiving section 74 having the base thereof coplanar with upper terminal rim 78 of the connector section which abuts the lower surface of the piercing device assembly when operatively assembled thereon. A connector transition section receiving portion 80 is frusto-conically shaped and has the base thereof integrally connected to the frustum of the connector base receiving station. As shown in FIG. 1, when the piercing device assembly is connected to the observation chamber, the spike 26 is snugly received within bore 68 of the connector section.

A port section 90 has a tubular body 92 mounted on bulkhead 59 to depend downwardly therefrom into bore 58 of the observation chamber. The frustum of the portion 80 has a fluid passage 94 defined therein to receive fluid from the port 40 when the spike is accommodated within the connector section. A tip section 96 is mounted on the lower end of the body 92 to depend therefrom into the observation chamber bore 58. The tip section has a lower terminal end having a port means thereon. In the preferred embodiment, this port means comprises a metering orifice 100, and the tubular body 92 has a bore 104 defined axially therethrough which fluidly connects fluid passage 94 to the metering orifice 100, so that fluid dispensed from the source passes into the observation chamber via the metering orifice.

The metering orifice 100 is preferably sized to pass 60 drops per milliliter therethrough. When the orifice 100 is superposed onto orifice 42, the flow rate into the drip chamber is determined by the flow rate through orifice 100, and hence, it is 60 drops per milliliters in the preferred embodiment.

The metering orifice 100 functions in the usual manner, wherein the rate and character of fluid passing through that orifice depends upon the orifice size and shape and the differential pressure established across the orifice. Thus, once orifice size and shape are fixed, flow through that orifice is established according to the difference between pressure existing upstream of the orifice and the pressure existing downstream of the orifice. The upstream pressure is a function of the fluid and the amount thereof in the source as well as conditions established in the flow path through the piercing assembly. The downstream pressure, also referred to herein as the back pressure, is a function of the conditions established in the drip chamber assembly.

A radially extending, circumferentially disposed rim 110 is mounted on the tubular body 52 near lower end 56 and serves as a limit stop as will be discussed below, and the observation chamber is formed of a stiff material, such as plastic or the like, for a purpose which will also be discussed below.

The drip chamber assembly further includes a tubular pump chamber section 120 having an axial bore 122 extending therethrough from top end 124 to bottom end 126 fluidly connecting those ends together. As will be discussed below, the pump chamber is formed of a flexible material which has memory characteristics to return to an undeformed configuration after deformation thereof. The pump chamber has an inner diameter slightly greater than the outer diameter of the lower end of the observation chamber to receive that observation chamber in a telescoping and snug fit, as shown in FIG. 1. The upper rim 130 of the pump chamber abuts lower surface 132 of the limit stop rim 110 so that the observation chamber is joined to the pump chamber by an airtight lap joint-like fit.

The flexible pump chamber permits priming of the system, and provides a reservoir R of fluid during an empty bottle condition to prevent interruption of the flow immediately upon the occurrence of an empty bottle condition. By deforming the pump chamber manually, air is forced out of the drip chamber through the lower end. Upon release of the pump chamber, the material memory causes that chamber to return to the configuration shown in the Figures, whereby a suction is created and fluid is drawn through the metering orifice. The manual pumping operation is continued until the pump chamber is primed to the base of the observation chamber. As discussed above, priming the pump chamber to the base of the observation chamber causes pressure perturbations to be transmitted directly into the observation chamber.

The tube connector 16 is attached to the lower end 152 of the pump chamber and includes a body section 160 having an elongate tapering tip 162 depending therefrom. An axial bore 164 is defined through the tip 162 and a cylindrical boss 166 having an axial bore 170 defined therethrough is attached to the body section to extend upwardly with the axial bore 170 in fluid connection with the bore 164 to conduct fluid from the pump chamber into the tubing (not shown) via the tube connector tip. An annular collar 180 is positioned on the body section 160 and includes an outer upstanding member 182 circumferentially positioned on the body section 160 and an inner upstanding member 184 spaced from the outer member and from the boss 166 to define a slot 186 between the inner member and the outer member and a slot 188 between the inner member and the boss. The slot 186 is sized to snugly receive the lower end 152 of the pump chamber and securely couple the chamber to the connector 16 as shown in FIG. 1. An upstanding foraminous filter F is mounted on the boss 166 and is self-supporting within the pump chamber, as shown in FIG. 1. The filter is interposed in the fluid path between the pump chamber and the tube connector. Thus, in the operative configuration, the fluid path through the apparatus 10 includes the fluid path through the piercing device, the bore 42, port 40, bore 104, metering orifice 100, bore 58, pump chamber bore 122, filter F, bore 170, and bore 164. Accordingly, the fluid passes through the drip chamber assembly and the filter enroute to the tubing.

As discussed above, the flow through the metering orifice 100 is determined according to the size and shape thereof, as well as the differential pressure established thereacross. As indicated in FIG. 1, flow exiting the metering orifice is in the form of droplets D.

As can be seen in FIG. 1, the droplets traverse the observation chamber, then enter the pump chamber. As above-discussed, the pressure conditions established in the observation chamber directly influence the flow rate through the metering orifice as manifested in the rate with which droplets are formed and released from the metering orifice. Furthermore, the length of the observation chamber determines the length of time required for a pressure perturbation to traverse the observation chamber from the top of the reservoir to the metering orifice to effect formation of a liquid droplet, or to shut off flow through that metering orifice.

As was also discussed above, it has been determined that the volume of air in the drip chamber has a strong influence on drop rate, so that the air acts as a "cushion" when a drop falls, resulting in double and triple drops from a 60 drop orifice.

Thus, from the above discussion, it can be seen that overall flow rate through the system can be controlled by controlling the volumes in the drip chamber.

As was discussed above, the abrupt change in cross-sectional area, or volume per unit length change, occurring at the joint between the observation and pump chambers causes pressure perturbations created by changes in liquid level in the reservoir to be stronger at the metering orifice than if such abrupt area change were not present. The length of the observation chamber between the rim and the metering orifice is selected so that the pressure perturbation caused by a droplet being added to the reservoir in response to a demand by the overall system downstream of the apparatus traverses the distance between the reservoir and the metering orifice in time to stop flow through the orifice prior to formation of a further droplet after the first droplet is formed. In the preferred form, the observation chamber is tubular with the rim 200 chamfered on the inner surface thereof at a 30 degree angle, and has an inner diameter of 0.285 inches, an outer diameter of 0.385 inches, a length from the lower surface of the rim 200 to the metering orifice of 0.650 inches. The metering orifice 100 can be a size suitable for producing 60 drops per milliliter and has a diameter of 0.02 inches. In the preferred embodiment, the pump chamber has an inner diameter of 0.500 inches and an overall length from rim 130 to rim 202 of 1.5 inches. If the observation chamber has a length of 0.25 inches between the lower surface of the shoulder 110 and the lower rim 200, the effective length of the reservoir (when full) will be approximately 1.25 inches, or the distance between the lower rim 200 and the inner surface of the tubing adaptor. With these dimensions, an air volume of 0.65 cubic centimeters is established in the observation chamber beneath the metering orifice. Flow control is especially pertinent to the electronic controlled devices, such as disclosed in the referenced Burke patents, wherein electronic timing equipment controlling flow control valves in the system is triggered by droplets falling through the drip chamber. Multiple drops falling through the drip chamber may cause mismanagement of the associated electronically controlled vlaves, thereby vitiating the control of the fluid flow rate by the electronic equipment. Thus, precise control over droplet formation rate should be effected to produce concomitant precise control over flow rate from the system in both electronically and manually controlled systems.

The air volume in the preferred embodiment of the present invention is reduced from 2 cubic centimeters of air below the orifice as presently used in the prior art to 0.65 cubic centimeters of air below the orifice. It has been determined that the lower air volume results in exact control over drop rate and effectively prevents the above-discussed multiple drop problem. Thus, in conjunction with a 60 drop per milliliter orifice, the 0.65 cubic centimeter air volume produces the single drop flow required for proper flow management by electronic equipment, such as that disclosed in the aforementioned Burke patents.

The observation chamber is of rigid construction with the limit stop shoulder formed at a location to produce a drip chamber having a proper volume when the observation and pump chambers are joined together. From a manufacturing standpoint, it has been found to be most efficient to construct the observation chamber separately and of rigid material, and then join that chamber to the flexible pump chamber during system setup.

Alternative embodiments of the present invention are shown in FIGS. 4 and 5, wherein the drip chamber is a unitary one-piece molded construction with a transition section 300 between the observation and pump chambers. In FIG. 4, the upper connector section is omitted, and hence flow rate into the drip chamber is entirely dependent upon the size of the metering orifice 42, which in the preferred form of the piercing point assembly is 20 drops per milliliter. However, other orifice sizes can be used, or even other forms of the fluid passage can be used, without departing from the teachings of the present invention. The FIG. 5 embodiment is similar to the preferred embodiment except that the drip chamber is of unitary construction. The abrupt change in volume per unit length is still present in the FIGS. 4 and 5 embodiments, and the pump chamber is filled with fluid to a lower level 302 of the transition section so that the pressure perturbations caused by changes in liquid level of the reservoir are directed into the observation chamber without traversing any significant part of the pump chamber which would, as above discussed, tend to damp out those perturbations and result in a possibility of forming a subsequent droplet at the metering orifice 100 before a first drop reaches the surface of the reservoir. The length of the observation chamber in the FIGS. 4 and 5 embodiments is also selected so that the droplets reach the surface of the reservoir in proper sequence with the flow demands of any system control means.

It is, therefore, evident from the above discussion that the drip chamber provides sufficient volume to permit efficient priming while at the same time provides an apparatus with an air cushion small enough to result in only single drop formation and flow during a chosen cycle. Thus, the accuracy advantages of an electronic control system are retained while ease of manufacture and use are also provided by the drip chamber embodying the teachings of the present invention.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

We claim:

1. A connecting apparatus for use with infusion and transfusion systems comprising:
    a piercing device assembly for connection to a source of fluid;
    a tubing adaptor for connection to a length of tubing; and
    a drip chamber assembly connecting said piercing device assembly to said tubing adaptor, said drip chamber including an observation chamber having port means located at one end thereof through which fluid passes from said piercing device directly into said drip chamber, said observation chamber being attached to said piercing device assembly at said one end to form a joint and having defined therein an observation chamber passage through which fluid from the source of fluid passes directly from said source, a flexible pump chamber attached to one end thereof directly to another end of said observation chamber and receiving fluid directly therefrom, said pump chamber being filled with fluid at least and only to the level of said joint to form a reservoir from which fluid is removed during an infusion or transfusion procedure, said reservoir being located essentially entirely below said observation chamber, the removed fluid being replaced from the source of fluid as fluid is removed from said reservoir, said observation chamber being connected to said pump chamber so that a lowering of liquid level of said reservoir caused by removal of one drop of fluid from said reservoir causes a drop in pressure in said observation chamber sufficient to cause a formation of a replacement drop of fluid in said port means, said observation chamber having a cross-sectional area of about 0.4 square centimeters and having a length of about 1.6 centimeters, and said pump chamber having a cross-sectional area of about 1.3 square centimeters so that a liquid level change of said reservoir in said pump chamber effected by the replacement drop will cause pressurization of air in said observation chamber sufficient to prevent falling of a subsequent drop of fluid from said port means until the liquid level in the reservoir is again decreased by a further removal of fluid therefrom.

2. The apparatus of claim 1, further including an abutment shoulder on said observation chamber for abutting said pump chamber one end.

3. The apparatus of claim 1, further including a filter in said pump chamber for filtering fluid passing therethrough into the tubing via said tubing adaptor.

4. The apparatus of claim 1, wherein said observation chamber is rigid.

5. The apparatus of claim 1, wherein said port means includes a metering orifice.

6. The apparatus of claim 5, wherein said metering orifice is sized to pass 60 drops per milliliter.

7. The apparatus of claim 1, wherein said drip chamber is an integral one-piece construction and includes a transition section between said drip chamber and said observation chamber.

8. The apparatus of claim 1, wherein said piercing device has an exit port means thereon.

9. The apparatus of claim 8, wherein said exit port means includes a metering orifice.

10. The apparatus of claim 6, wherein said metering orifice is sized to pass 60 drops per milliliter therethrough.

11. The apparatus of claim 1, wherein said observation and pump chambers are tubular.

* * * * *